United States Patent
Turtzo

[11] Patent Number: 5,961,477
[45] Date of Patent: Oct. 5, 1999

[54] ANKLE/FOOT ORTHOSIS

[76] Inventor: Craig H. Turtzo, 2637 Westview Ct., Clearwater, Fla. 33761

[21] Appl. No.: 09/075,296

[22] Filed: May 8, 1998

[51] Int. Cl.[6] ....................................................... A61F 5/00
[52] U.S. Cl. .................................. 602/27; 602/12; 602/23
[58] Field of Search .................................. 602/10–12, 23, 602/27–29

[56] References Cited

U.S. PATENT DOCUMENTS

| | | |
|---|---|---|
| 3,976,059 | 8/1976 | Lonardo . |
| 4,057,056 | 11/1977 | Payton . |
| 4,178,925 | 12/1979 | Hirt ............................................ 602/11 |
| 4,587,962 | 5/1986 | Greene et al. . |
| 5,020,620 | 6/1991 | Bodine . |
| 5,050,620 | 9/1991 | Cooper . |
| 5,154,695 | 10/1992 | Farris et al. ............................... 602/27 |
| 5,250,021 | 10/1993 | Chang . |
| 5,329,705 | 7/1994 | Grim et al. . |
| 5,368,551 | 11/1994 | Zuckerman ................................ 602/23 |
| 5,372,576 | 12/1994 | Hicks . |
| 5,421,822 | 6/1995 | Wang . |
| 5,425,701 | 6/1995 | Oster et al. ................................ 602/23 |
| 5,460,600 | 10/1995 | Bieling . |
| 5,464,385 | 11/1995 | Grim . |
| 5,569,173 | 10/1996 | Varn . |
| 5,569,174 | 10/1996 | Varn . |
| 5,593,383 | 1/1997 | DeToro . |
| 5,609,570 | 3/1997 | Lamont ...................................... 602/65 |
| 5,620,411 | 4/1997 | Schumann et al. ........................ 602/23 |
| 5,735,805 | 4/1998 | Wasserman et al. ...................... 602/10 |
| 5,762,622 | 6/1998 | Lamont ...................................... 602/65 |

*Primary Examiner*—Michael A. Brown
*Assistant Examiner*—Kim M. Lee
*Attorney, Agent, or Firm*—Greensfelder, Hemker & Gale, P.C.

[57] ABSTRACT

A foot and ankle orthosis is adapted for use by a patient in both resting and walking modes. The orthosis includes a generally L-shaped support member which has a leg portion positioned behind the patient's lower leg, a heel portion positioned behind the patient's heel and Achilles' tendon area, and a foot portion positioned substantially entirely against the sole of the patient's foot, when in normal operative use position. The foot portion has an upper surface and a lower surface and the heel portion connects the leg portion and the foot portion. A walking sole plate is releasably connectable to the generally L-shaped support member, to thereby permit optional use by the patient of the walking sole plate in combination with the generally L-shaped support member for facilitating ambulation by the patient. A manually operable locking mechanism is attached to the lower surface of the foot portion of the generally L-shaped support member, to thereby permit rapid, selectively; releasable connection of the walking sole plate to the generally L-shaped support member.

21 Claims, 8 Drawing Sheets

ANKLE/FOOT ORTHOSIS

FIELD OF THE INVENTION

The present invention relates generally to the field of orthotic devices, and, more specifically to an ankle and/or foot orthosis having a selectively removable and replaceable sole plate which permits the user to quickly and easily adapt the orthosis for walking purposes.

BACKGROUND OF THE INVENTION

A variety of medical conditions require afflicted individuals wear a brace, cast or some type of orthotic to accommodate and support the foot and ankle. The present device is intended particularly for people with a condition commonly referred to as "foot drop", as well as being for ankle and foot weaknesses and instability which may be brought on by any number of causes, including traumatic injury and disease.

Previously, a variety of appliances have been attempted for use with such conditions, with varying degrees of success. Common problems with the known art include: (1) difficulty in obtaining an appropriate fit, so that tissue irritation occurs, as well as misplacement of pressure on certain areas of the foot, ankle and/or associated leg, (2) inability of the wearer to ambulate, (3) tissue irritation caused by the material of the devices (4) discomfort caused by a large appliance attached to the foot and ankle, even when the wearer is resting; (5) difficulty in putting on and removing the appliance; and (6) some known devices have been quick to wear out or break, causing increased expense, inconvenience, and even risk of injury to the wearer. Known foot and ankle orthotic devices were generally either for ambulatory use only or non-ambulatory use only, not both. In other words, an orthotic designed to permit the user to walk was not adaptable for comfortable wearing while reclining, and vice versa. The following art provides examples:

U.S. Pat. No. 5,050,620, which issued to Cooper, discloses a padded ankle brace adjustably connected with hook and loop fastener straps. However, the Cooper brace is not adaptable to accommodate walking. The patent which issued to Chang, U.S. Pat. No. 5,250,021 shows a foot and ankle brace which is much more substantial than the Cooper device, and includes a shoe base and rigid supporting sides to resist twisting and rotational torque to the user's leg. The arch portion of the Chang device is adjustably connected by hook and loop fastener straps and the walking sole is formed to permit rocking motion, but is not removable in the manner of the present invention.

The patent which issued to Green et al., U.S. Pat. No. 4,587,962 discloses a tibia/ankle orthosis with a supporting jacket which can be tightened without applying too much torque to the patient's leg and supporting the foot during the process of the application. The Green et al. device is not adaptable for a walking-type splint, nor is it fully padded as is possible with the present orthosis. Similarly, the Lonardo device, (U.S. Pat. No. 3,976,059 discloses a simple L-shaped splint with hook and loop strap attachments and optional extensions to protect the supine user's toes from sheets and bed clothes. Lonardo also does not teach any adaptation of the splint for walking.

Two patents issued to Grim/Grim et al, (U.S. Pat. Nos. 5,329,705 and 5,464,385) disclose a rigid sole platform and rigid braces, which extend upwardly on each side of the user's leg. A padded liner is provided and an optional insole to help prevent sores from forming. A cushioned non-removable rocker sole is also disclosed, as is a walker devise with an open heel, to permit better air access to the foot, and air bladders, which can be selectively inflated.

Although the art reveals orthoses which have removably connected walking soles, none are structured as in the present case, for rapid and facile attachment and detachment of the walking plate by the user, without assistance from others or the use of tools, nor the combination of such advantages with other features of the present device. Examples of previous devices, which all have some form of an L-shaped ankle and/or foot splint, include the following:

The patent which issued to Hicks (U.S. Pat. No. 5,372, 576) shows a padded therapeutic foot orthosis which, although having padding to cover the hard structures and protect the foot, does not connect the padding over the brace structure in the same manner presently proposed, with the rear pockets and an underfoot pocket with square cutout to accommodate the sole attachment mechanism. There is also no disclosure of attachment of the wrap to the brace in the manner presently described. In the patented Hicks brace, the leg extending portion and the foot supporting portion of the brace are each provided with a knurled edged nut and bolt arrangement for purposes of adjustable connection of a toe support extension portion which is connected beneath the rigid foot support.

A similar use of a nut and threaded bolt-in-slot arrangement is used in Bodine to attach a stabilizing/connecting bracket to the rigid leg support member of a foot and leg splint. However, Bodine does not disclose any walking sole.

The patent which issued to Wang (U.S. Pat. No. 5,421, 822) discloses a complex and heavy apparatus for rehabilitating an injured leg, particularly the calf portion thereof. This patent discloses a means of connecting a very heavy, complex sole plate which is much more complicated and time consuming in use than the new structure for a foot and ankle orthosis with an optional walking sole, as described and claimed herein.

The patent that issued to Bieling (U.S. Pat. No. 5,460,600) for a universal foot splint shows a method for connecting a toe extension unit to the bottom of the splint. The apparatus includes a threaded nut and bolt arrangement in which an elongated track slideably receives the extension member and can be tightened down on the extension member after the nut and bolt arrangement is placed appropriately. Although the Bieling locking mechanism includes a turning member, there is no essentially fixed placement of the connection arrangement, as in the present case. Rather the Bieling extension member is slideable and does not appear to include any padding for comfort and tissue protection during walking, but rather has only a limited amount of padding for support for the foot and toe during recovery.

The patent which issued to Payton (U.S. Pat. No. 4,057, 056) discloses a walking cast with a removable sole. Although the Payton cast includes an "L" shaped rigid support member which travels behind the leg and under the foot, and an over-wrap member which is adjustably applied with hook and loop fastener straps, it varies substantially from the present device in a number of ways. The deep rocker sole of Payton is attached by moving it transversely with relation to the bottom of the foot and connecting it beneath the arch of the foot with a tongue and groove style attachment, as well as by connecting the toe portion of the sole. Further, the over-wrap of Payton is more complex and time consuming to apply, having a front portion which is completely independent from the back and side portions of the wrap and which is connected therethrough by laborious threading of the connection straps through a plurality of rings on each side of the front portion.

A patent which issued to DeToro (U.S. Pat. No. 5,593,383) for a foot and ankle brace includes an "L" shaped construction with contoured leg support portion and a foot portion and a fabric padding which connects by straps. However, it does not show a quickly attachable and detachable walking sole which extends outwardly forwardly under the toes of the user, beyond the end of the rigid "L" shaped portion, nor the overall fabric construction which connects to the brace as in the present invention. In DeToro, the walking pad terminates forwardly under the ball of the foot and the toe portion is supported by the continuation forwardly of the rigid "L" shaped portion.

The Varn U.S. Pat. Nos. 5,569,173 and 5,569,174 both feature a foot orthosis with a detachable sole plate. The '173 patent shows an L-shaped leg and foot support member. A nut and bolt arrangement extends downwardly and attaches the sole portion to the toe extension portion. A optional walking pad can also be added beneath the rigid foot support portion by hook and loop strips attached, as by adhesive, to the top of the walking sole and the bottom of the foot support portion, and a hole is provided to receive the downwardly extending nut and bolt plate attachment. This nut-receiving opening in the sole in Varn does not serve as part of the walking sole connection, as in the present case. Rather, it serves to connect the toe-protection extension. This structure is seen also in Varn patent '174. Again, connection of the rubber walking sole is by hook and loop fastening straps.

By contrast, the device of the present invention permits both ambulatory and non-ambulatory functions, and is designed to permit quick and easy alteration of the device from one mode to the other in a manner heretofore unknown, along with a variety of other advantageous features in a single, economical and comfortable foot/ankle orthosis.

SUMMARY OF THE INVENTION

In order to overcome the shortcomings of known ankle and foot orthotics, the present invention has been developed with a number of goals in mind. The device features a number of advantages, key among which is the adaptation of the walking sole portion of the device for quick and facile removal and replacement by an unassisted individual, without the use of any tools. This is accomplished in and ankle/foot orthosis ("AFO") which at least meets, and frequently exceeds, Medicare guidelines for durability (lasting a minimum of six months).

It is further among the features of the present invention, having the advantages indicated, that the new device be formed so as to accommodate the wearer's foot without causing pressure to be applied to the heel, and that the materials of the device include a soft, anti-microbial interface and a soft, comfortable, breathable and launderable liner, which serves to attach the orthosis to the wearer, as well as to cushion the wearer's tissues from contact with the material of the appliance. Moreover, the construction of the new ankle/foot orthosis relieves pressure from the ball of the wearer's foot during ambulation, while also providing sufficient arch support.

Accordingly, in furtherance of the above features and advantages, the present device is, briefly, a foot and ankle orthosis adapted for use by a patient in both resting and walking modes. The orthosis includes a generally L-shaped support member which has a leg portion positioned behind the patient's lower leg, a heel portion positioned behind the patient's heel and Achilles' tendon area, and a foot portion positioned substantially entirely against the sole of the patient's foot, when in normal operative use position. The foot portion has an upper surface and a lower surface and the heel portion connects the leg portion and the foot portion. A walking sole plate is releasably connectable to the generally L-shaped support member, to thereby permit optional use by the patient of the walking sole plate in combination with the generally L-shaped support member for facilitating ambulation by the patient. A manually operable locking mechanism is attached to the lower surface of the foot portion of the generally L-shaped support member, to thereby permit rapid, selectively; releasable connection of the walking sole plate to the generally L-shaped support member.

The invention also includes, briefly, a cover formed of a plurality of flexible material sections connected together as a single unit and shaped to cover substantially all of the patient's foot, but leaving the toes free and unencumbered.

BRIEF DESCRIPTION OF THE DRAWINGS

Throughout the drawings like parts are indicated by like element numbers.

DESCRIPTION OF THE PREFERRED EMBODIMENT

Figure 3:
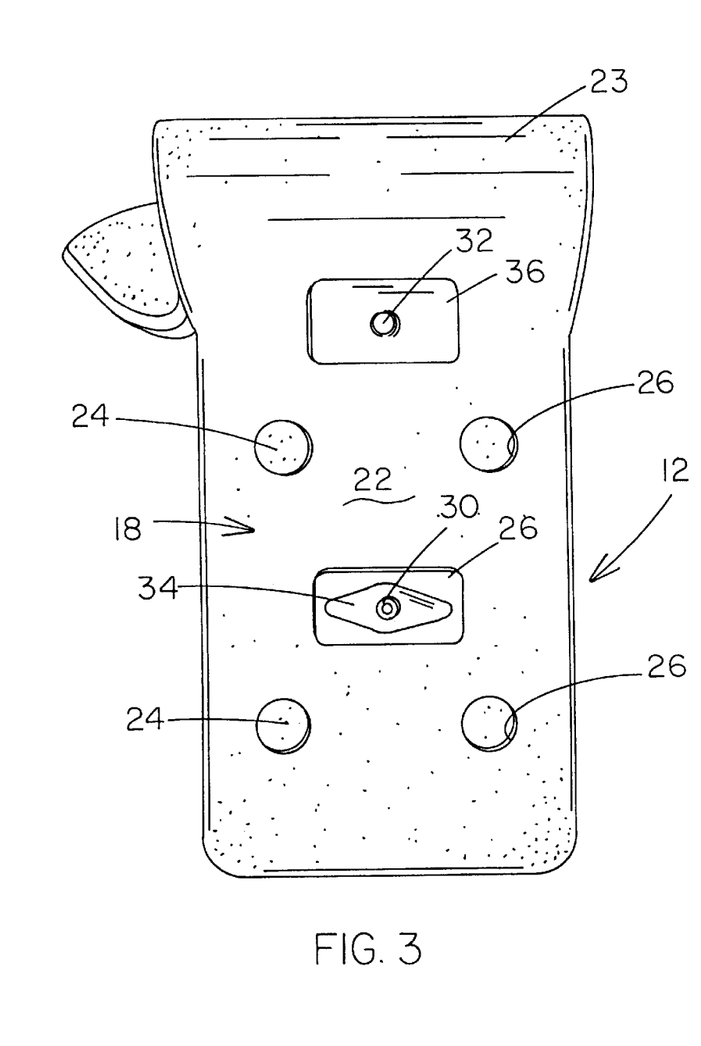
FIG. 3 is a bottom perspective view of the device of FIG. 1, without the sole plate.
Figure 3A:
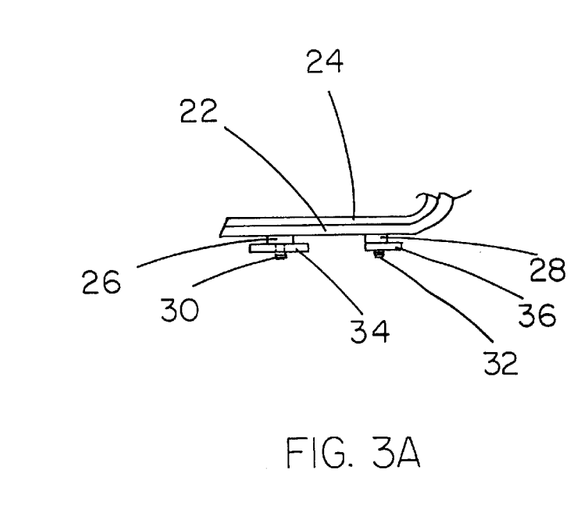
FIG. 3A is a partial, schematic, side elevational view of the splint portion of the device of FIG. 3, reduced.
Figure 4:
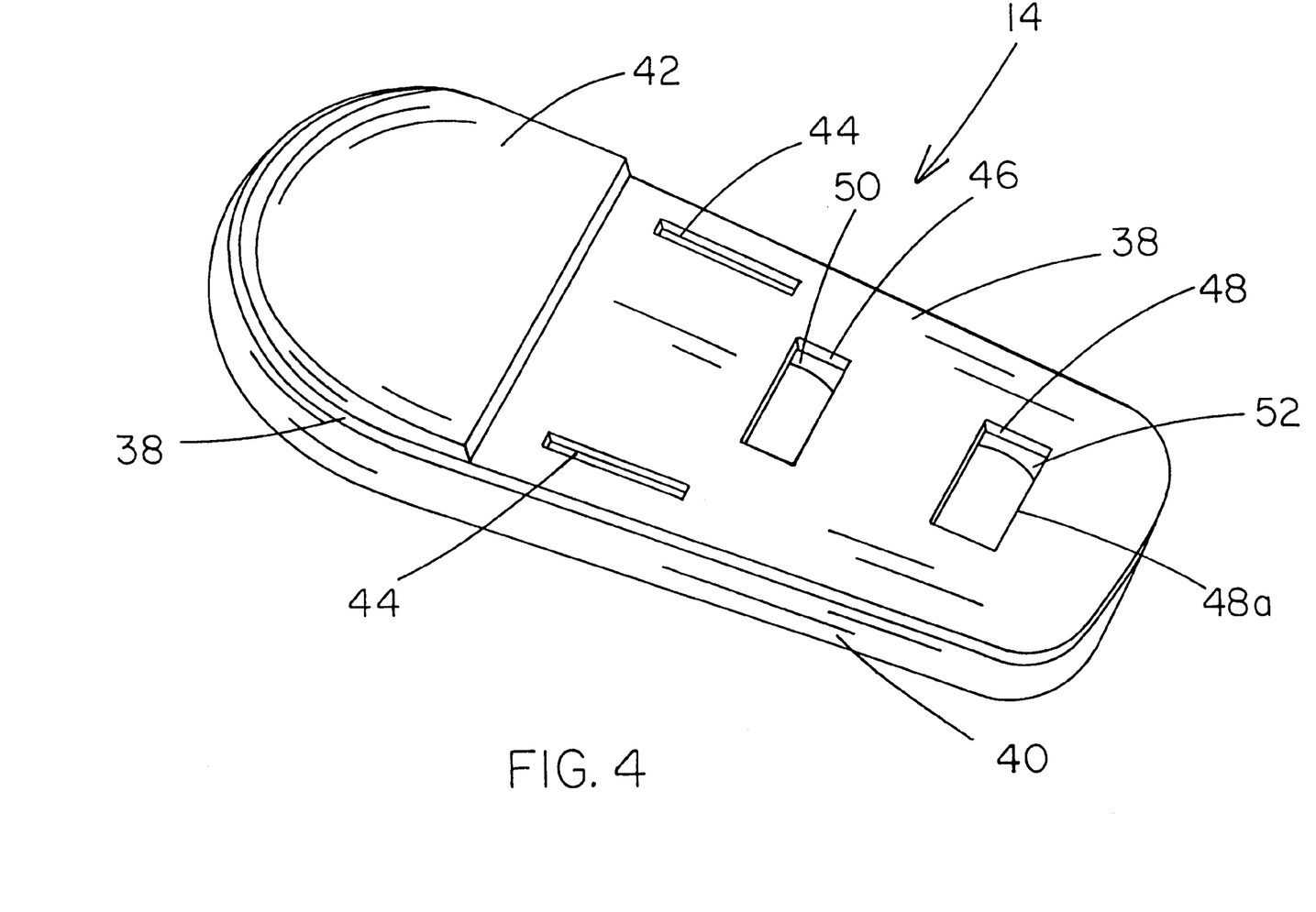
FIG. 4 is an upper perspective view of the sole plate of the device of FIG. 1.
Figure 5:
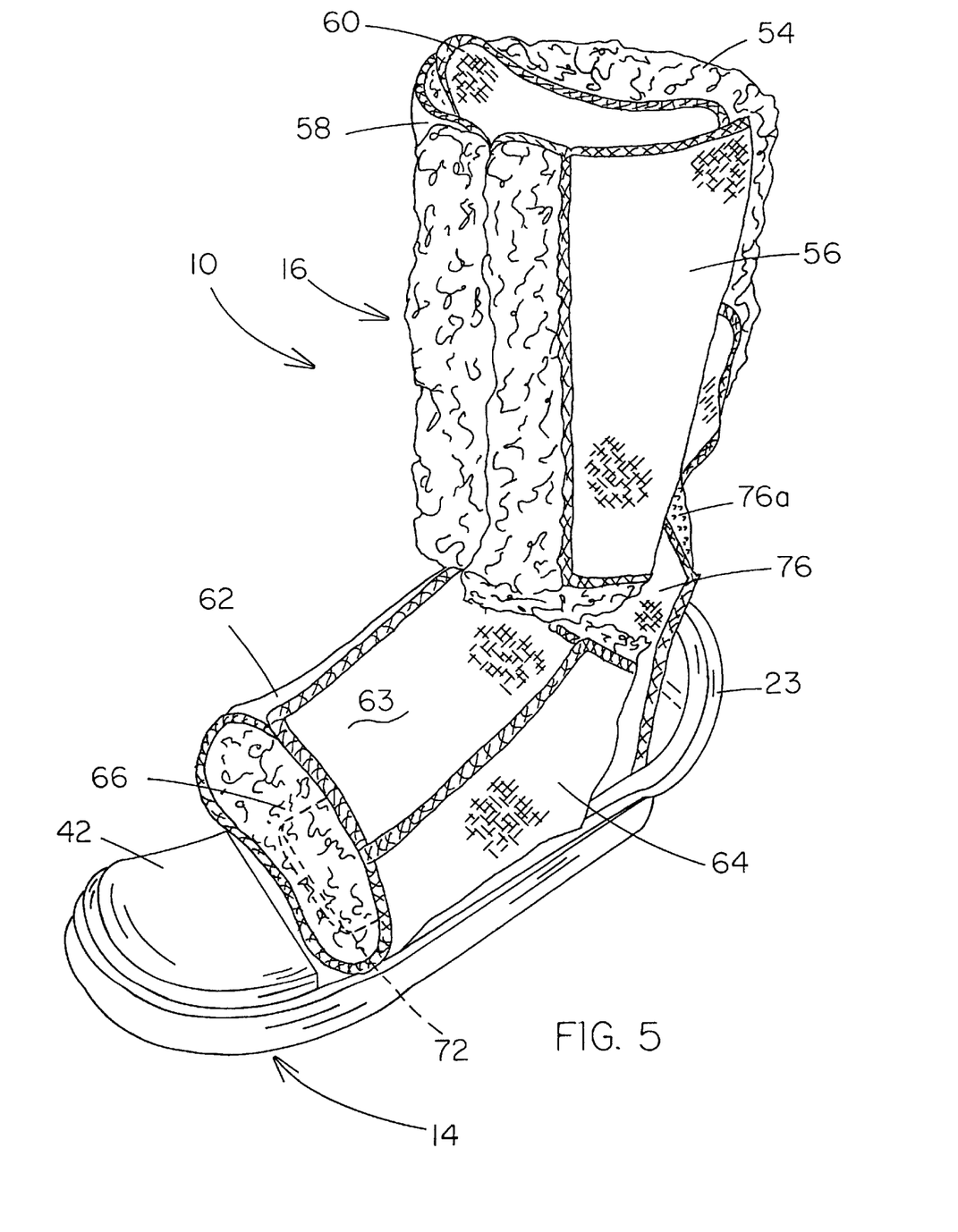
FIG. 5 is the upright perspective view of the orthotic device of FIG. 1 with an optional cover in normal use position on the device.
Figure 6:
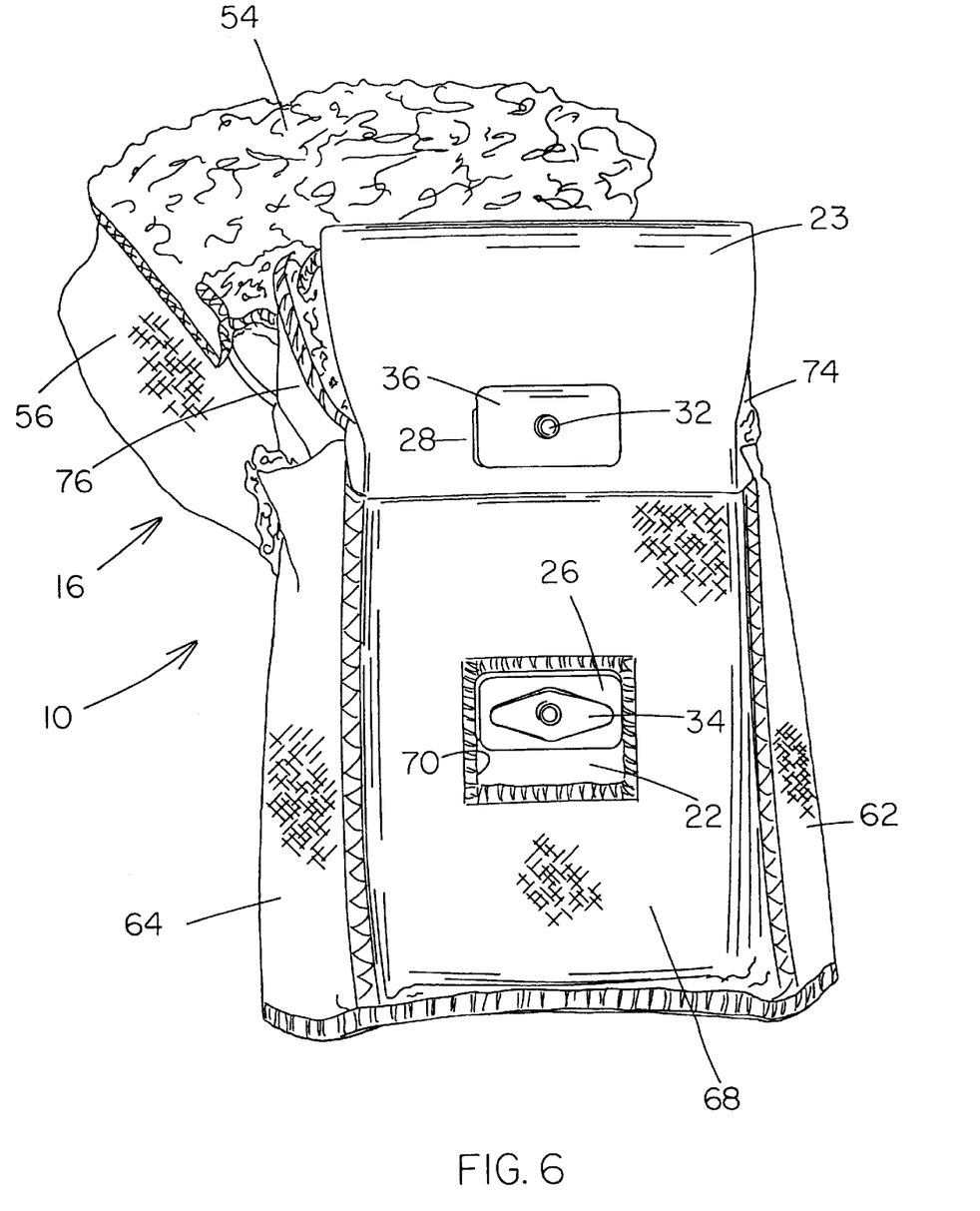
FIG. 6 is the device as shown in FIG. 3, but with the option cover attached.

With reference to the drawings, and especially FIGS. 1–4, 10 generally designates a foot and ankle orthosis (or orthotic device) consisting generally of an L-shaped foot and ankle support, splint or upright member 12, a sole or walker plate 14 which is selectively detachably connectable with relation to L-shaped member 12 and a specially designed cover portion 16, which is illustrated positioned on device 10 in FIGS. 5 and 6. An optional flat toe protector plate 15 is shown schematically only, in FIG. 14 and is provided as a non-walking sole plate extension which, connected to the support member as described with reference to the walking sole plate, passes under the toes and serves merely to protect the wearer's toes from the pressure of bedclothes, etc. when device 10 is not adapted with the walking sole.

L-shaped support member 12 of device 10 includes an outer shell 18 of the device, which shell is preferably formed by molding of a strong, rigid plastic material, such as, for example, the fire retardant plastic sheeting used in aircraft interiors and sold under the trademark KYDEX (registered to Kleerdex Company) or other similar, suitable substance. Shell 18 of L-shaped member 12, when considered in a position as for walking, as in FIG. 1, has an upright or leg portion 20 which is molded or otherwise formed to a shape which conforms generally to the calf, ankle and back of the heel of the wearer, and includes smoothly curved corners for comfort and safety. Upright portion 20 extends continuously from the upper or calf end downwardly to the heel end and there intersects a flat foot support portion 22 which extends forwardly a sufficient distance to terminate beneath the ball of the wearer's foot, but preferably not so far as to extend beneath the wearer's toes.

Accordingly it is intended that device 10 be made available in a variety of sizes, suitable for men, women and children of various ages, in order to most readily attain the therapeutic goals. The heel portion 23 curves rearwardly between the lower end of upright 20 and foot portion 22 in order to generously spatially accommodate the wearer's heel. In the preferred embodiment illustrated the degree of curve is great enough that heel portion 23 is sufficiently offset from upright portion 20 that the wearer's heel and Achilles' tendon will not be in resting contact with the inner surface of device 10. This heel pressure relief is due in part to the wearer's calf contacting the inside of upright portion 20 (and the interface lining same) and thereby causing the heel to be urged forwardly away from the inside of heel portion 23. Heel pressure relief is provided further by the addition of cover 16 and specific features thereof, which will be hereinafter more fully discussed. FIG. 3 most clearly shows that heel portion 23 of shell 18 (and thus of L-shaped member 12) is also substantially wider than the leg portion 20 at the lower end thereof just behind the wearer's Achilles' tendon, and wider than the foot portion 22, thereby providing extra protection for the foot and ankle area of the patient.

A soft, flexible lining or interface 24 having a substantially uniform thickness throughout conforms to the shape of the inside (the foot and leg side) of shell 18, and is fixed contiguously thereto, as, for example, by a suitable adhesive. Interface 24 is preferably formed of a known, antibacterial material, such as, for example, a polyurethane/visco-elastic polymer, or expanded polyolefin foam sheeting. One such known suitable material is that sold under the registered trademark VOLARA (owned by Sekisui America Corporation). Of course other available materials can be suitably substituted for interface 24, as long as such materials serve the purposes of providing some padding between the user's skin and the rigid material of shell 18 and reduces pressure on the ball of the user's foot during ambulation.

FIG. 3 illustrates a plurality of optional apertures 26 which are formed through foot portion 22 of shell 18 for purposes of assisting in the molding process, as well as serving to lighten shell 18 and provide air flow to permit moisture escape from pad/lining 24, which moisture would otherwise encourage bacterial and fungal growth over extended wearing periods.

Figure 2:
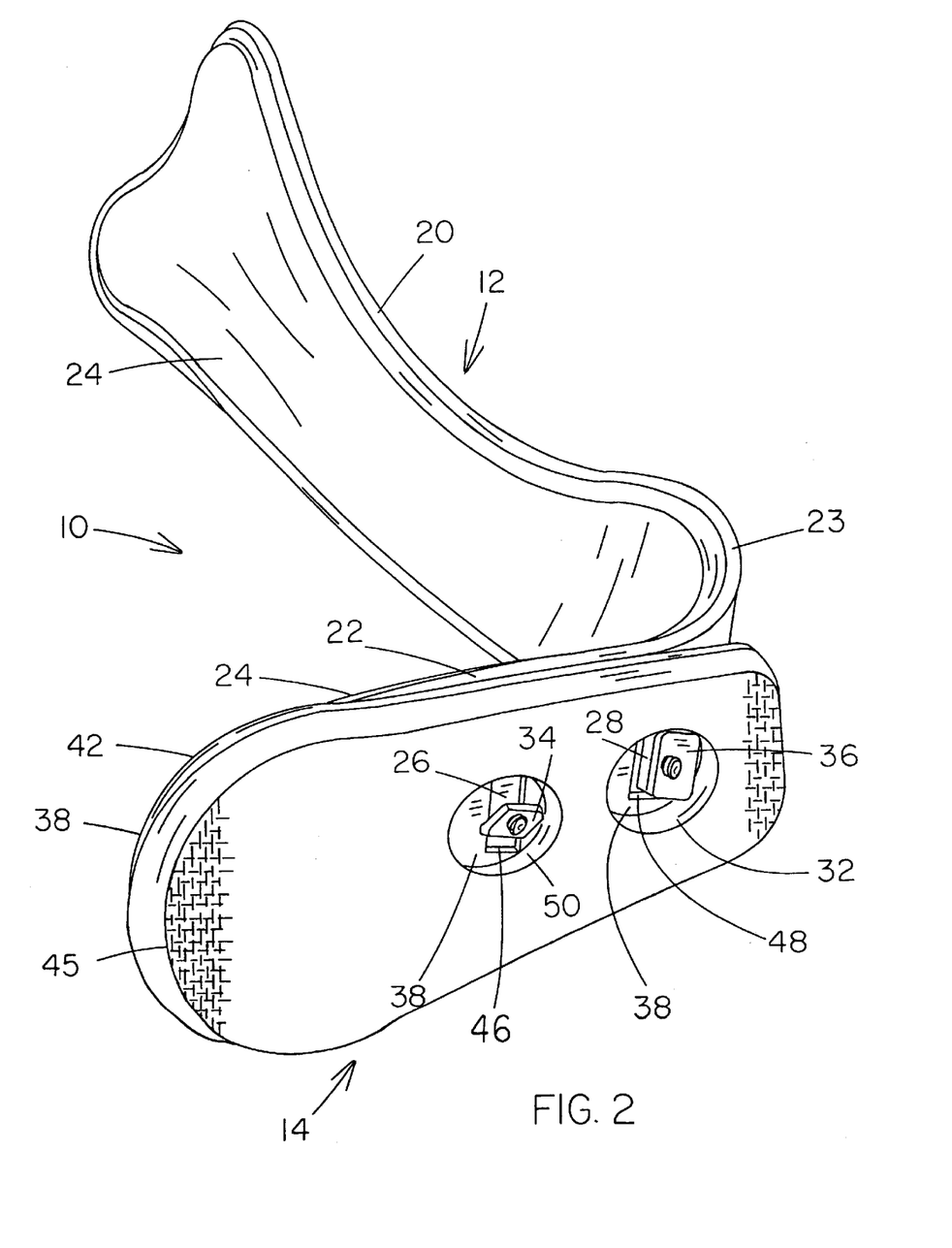
FIG. 2 is a bottom perspective view of the orthosis of FIG. 1 with the sole plate attached.

FIGS. 2 and 3A illustrate the preferred structure by which sole plate 14 is selectively and releasably connected to the outside of foot portion 22 of L-shaped support member 12. Fixed by known means, such as by gluing or bolting, to the bottom surface of foot portion 22 of splint 12 are a pair of base plates 26, 28. Base plates 26, 28 are preferably, although not necessarily, substantially equal in size and shape, being generally rectangular and formed of metal or other similar strong material, and disposed parallel to one another, transversely along the longitudinal axis of foot portion 22, and each having a threaded shaft 30, 32, respectively, or other equally useful connector extending downwardly, and substantially centrally therefrom.

Rotatably mounted on shaft 30 is an elongated locking member or key-nut 34 which interacts with a portion of sole plate 14, as described further hereafter, to selectively releasably secure sole plate 14 to the forwardly directed end of foot portion 22 of splint 12. A further rectangular plate 36 is secured by connector 32 to base plate 28, at the rearwardly directed end (heel end) of the bottom of foot portion 22. The forwardly directed edge of plate 36 is preferably substantially flush with the forwardly directed edge of base plate 28, as shown in FIG. 3A. Plate 36 has substantially the same length and depth as base plate 28, but is sufficiently wider (larger in the mounted position, along the longitudinal axis of foot portion 22 of splint 12) to have a stepped appearance in side view (FIG. 3A).

The rearwardly directed edge of plate 36 extends from base plate 28 sufficiently far to hook or "grasp" a portion of the sole plate, as further described, and thereby retain the heel end of the sole plate 14 to the heel end of the splint foot support portion 22. For optimal structural fit, the thickness of base plates 26, 28 is substantially the same as, or slightly greater than the thickness of semi-rigid footbed 38 of sole plate 14, so that the upper surface of retention plate 36 is spaced sufficiently far from the lower surface of foot support portion 22 to permit freely sliding receipt of edge 48a, described further hereafter.

Figure 1:
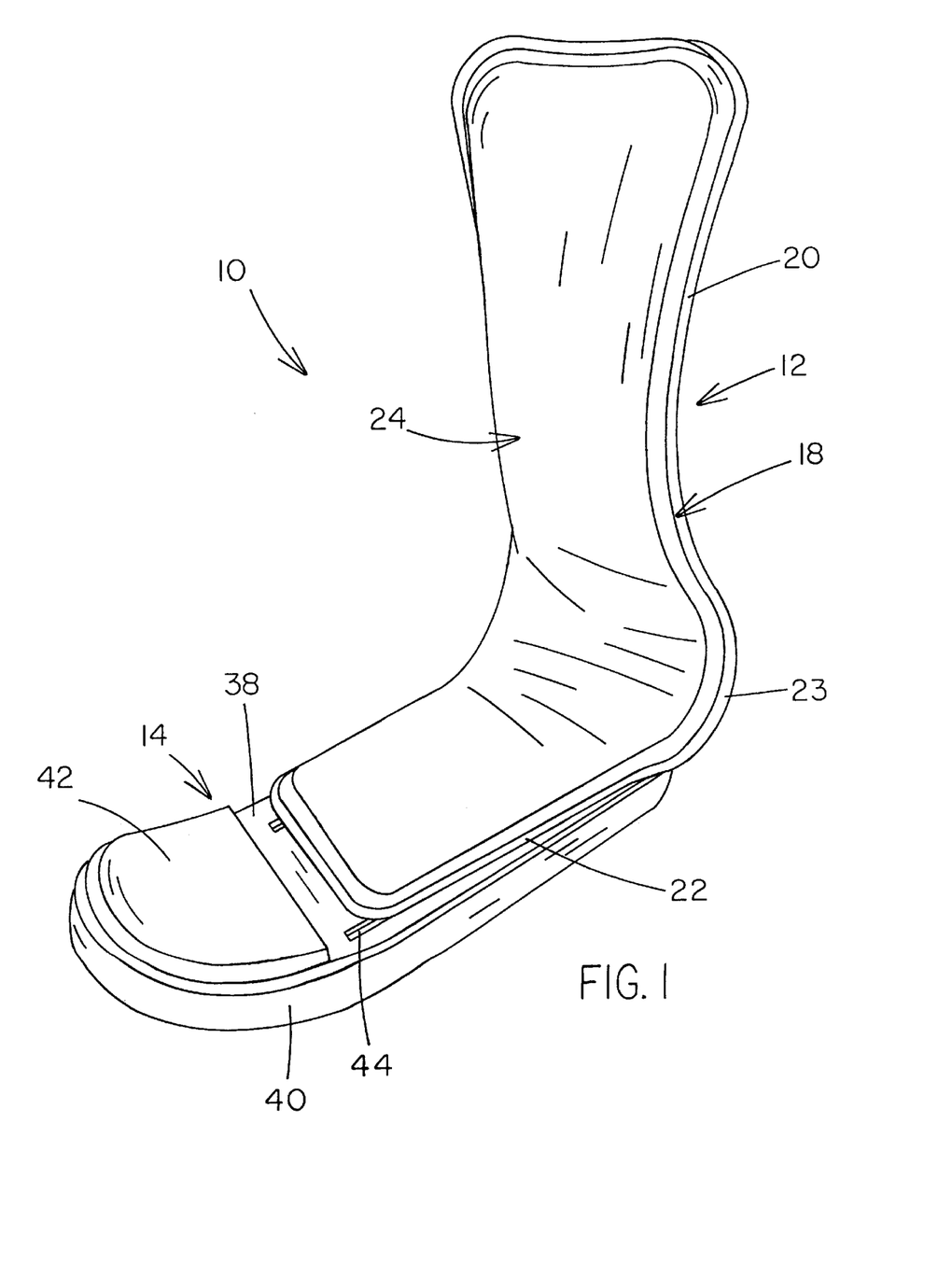
FIG. 1 is a front perspective view of an ankle/foot orthotic device, shown in an upright position and having a removable bottom or sole plate and constructed in accordance with and embodying the present invention.

FIGS. 1, 2 and 4 show walker sole or sole plate 14, which is composed generally of a hard plastic foot bed 38 and a thick rubber lower layer 40 affixed to the bottom surface of the foot bed. Foot bed 38 is elongated and generally wider at the front end than at the heel end, in order to accommodate the toes and ball of the user's foot. Like the L-shaped support/splint portion 12, sole portion 14 is provided in a variety of sizes in order to suit the needs of the user. Similarly, the material of which sole portion 14 is formed can also vary somewhat. However it is preferred that foot bed 38 be formed of the same semi-rigid material as splint 12, and that the thick, cushioning outer layer 40 be formed of neoprene rubber, or other equally durable, cushioning substance, which will provide shock absorption and a gridded or otherwise patterned non-slip bottom surface for patient safety during ambulation.

A cushioning lining member 42 (seen in FIG. 4) is desirably laminated onto or otherwise smoothly and contiguously fixed to the top surface of the forwardly directed, slightly upturned toe end of supporting foot bed 38 and is conformed to the perimeter shape of the front portion of the foot bed. Lining member 42 is formed of the same or similar material as is used in forming splint liner (interface) 24, so as to provide cushioning to the patient's toes during walking, and to also be antibacterial, to discourage the development of foot infections by the user.

Rearwardly of lining member 42 there are preferably formed in foot bed 38 at least two elongated channels 44, which are disposed substantially parallel to one another and extend entirely through the thickness of foot bed 38. Channels 44 serve to reduce the weight of foot bed 38 and to provide a somewhat enhanced "give" or flexibility to the ball area of the footbed to facilitate walking in AFO 10. Other constructions are of course conceivable which can be adequately substituted for channels 44.

FIG. 1 illustrates that when AFO 10 is assembled with L-shaped support member 12 connected to the top surface of walking sole 14 a limited length (in the order of approximately ½ to ¾ inch) of the top of foot bed 38 is exposed in a longitudinal gap between the forward end of splint foot support portion 22 and the rearward end of liner 42. The exposed area may or may not include portions of channels 44, depending upon the size of the foot bed and the length of the channels. Also, so assembled, the level of the upper surface of interface 24 on foot support portion 22 will necessarily be slightly higher, relative to the floor, when device 10 is in the upright, walking position, than the top surface of toe protection liner 42 on the forward end of foot bed 38. This feature provides the user's toe area with somewhat more space, for comfort, and to minimize chaffing and blistering.

Rearwardly of channels 44, and transversely disposed along the central longitudinal axis of foot bed 38 there are formed a pair of rectangular through holes 46, 48, which are adequately sized, shaped and sufficiently spaced apart from one another to receive base plates 26, 28, respectively, on the lower surface of foot portion 22 of splint 12. In FIG. 2 rectangular holes 46, 48 are seen within circular cutouts 50, 52, respectively, formed through rubber bottom sole 40. Circular cutouts 50, 52 are sufficiently large in diameter as to permit ready manual access to rectangular holes 46, 48 and the members on the bottom surface of support member 12 which connect member 12 to sole plate 14.

To connect sole plate 14 to splint 12, key nut 34 is positioned as shown in FIG. 3, transversely to the longitudinal axis of foot support portion 22. Then plate 36 is placed into rectangular opening 48 as base plate 26 and key nut 34 are placed into rectangular opening 46. Foot bed 14 is then shifted slightly forwardly relative to foot support portion 22, so than a rearward edge 48a of opening 48 (FIG. 4) is secured between the bottom surface of foot support portion 22 and the rear upper surface of plate 36. Finally, key nut 34 is turned approximately 90 degrees, to the position shown in FIGS. 2 and 3A, or otherwise along threaded shaft 30 until snug against base plate 26. In "locked" position, the opposed ends of key nut 34 extend generally longitudinally, beyond the parallel long sides of base plate 26, to thereby maintain sole plate 14 in secure connection to splint portion 12 for ambulation by the wearer.

FIG. 5 illustrates the new ankle/foot orthosis 10 in the upright position, fully assembled and in combination with a thick, cushioning cover 16, in the closed, normal use position. FIG. 6 shows device 10 in bottom perspective, with the walking plate 14 detached, for enhanced comfort of the user when sitting or reclining. The schematic views in FIGS. 7–14 provide further explanation of the portions of cover 16 and the use thereof. Although it is possible to make use of L-shaped splint portion 12 and walking sole 24 without the benefit of cover 16 (for example by connecting the splint to the user's leg by use of an elastic bandage, or the like), to achieve optimal benefits from new orthosis 10 the preferred structure for a cushioning over wrap is as shown and described hereafter, with reference to the figures and cover portion 16.

Generally, cover 16 is formed of a very thick, plush pile material, such as sheepskin or synthetic substitutes therefor, such as a blend of polyester and acrylic fiber, or other suitable substitutes, which are preferably "breathable" and washable. As illustrated in FIG. 5, it is preferred to form cover 16 so that in normal use position on orthosis 10 the thick pile side of the material is facing inward to permit contact with the user, for optimal comfort. However, other fabrics and materials conceivably will suffice, and use of the illustrated one-sided pile material in an inverted position is possible, although generally preferred.

The cover is constructed as a unit from various portions firmly connected to one another, as by stitching, for example, and formed so as to be easily slipped onto device 10 in such manner as to prevent contact between the user's foot, ankle, heel and any areas thereof which would otherwise become irritated from contact with the orthotic 10. Cover 16 can also be readily removed for laundering as may be necessary from time to time. Notably, the user's toes are not enclosed in cover 16, thereby permitting better improved air flow to the toes and foot within the covered device 10, and ready access to the toes for treatment, if necessary.

Generally, cover 16 includes a number of sections which are permanently joined together, and parts of some of which sections are adjustably, releasably connectable to each other, preferably by known hook and loop fastener strips, but alternatively by other suitable, known connectors. More specifically, in the preferred embodiment illustrated in FIGS. 5 and 6, and shown schematically in FIGS. 7–15, cover 16 is described with reference to its normal use position, releasably connected to or "mounted" on L-shaped support member 12 with the described interface 24 fixed thereto. Cover 16 is to be placed over L-shaped support member 12 prior to the attachment of sole plate 14 to the support member.

Cover 16 has a back leg section 54 which extends continuously from the front of splint leg portion 20 entirely up, over and down the back of splint leg portion 20. The longitudinal sides of back leg section 54 are joined, for example by stitching, for a substantial part of their respective lengths, from the top, downwardly, so as to form a pocket for sliding receipt of splint leg portion 20, with the closed end of the pocket being directed upwardly and the open end facing downwardly when the wearer is in normal standing position.

The opposed longitudinal sides of cover back leg portion 54 are each connected on the respective front sides thereof to side leg portions 56, 58, which side portions 56, 58 extend forwardly to protect the sides of the user's calf and terminate along the inside forward longitudinal edges thereof with a strip of (preferably) the hook portion of hook and loop fastener material, such as that generally known by the registered trademark, VELCRO for selectively releasable and adjustable connection to tongue portion 60.

Tongue portion 60 is sufficiently long to extend downwardly along the wearer's shin area and then continues forwardly over the top of the wearer's foot. The leg portion of tongue 60 is free and unattached along opposed longitudinal sides and is preferably provided on the outer surface thereof with the loop portion of hook and loop fastener material to thereby permit the patient or caretaker to securely and comfortably connect the side portions 56, 58 to the tongue portion longitudinal sides.

The forwardly directed foot—covering portion of tongue 60 provided on the upper (outer) surface with a patch 61 (indicated in phantom in FIG. 7) of hooked fastener material. One side of the tongue foot portion is connected, for example by stitching, to a generally rectangular foot side portion 62 which is of sufficient dimensions to cover the respective side of the wearer's foot, leaving the toes and ankle bone area uncovered. The opposite foot side portion 64 of cover 16 includes a lower section which is sized and shaped to correspond to foot side portion 62, but includes a free extension 63 which has on the inner surface thereof a patch 65 of looped fastener material. Extension 63 extends sufficiently far over the top of the wearer's foot (in normal use position) sufficiently to overlap portion 60 so that patches 61, 65 can be placed in contact with one another. In this manner foot portions 60, 62 and be adjustably and releasably connected quickly and securely as however may be necessary for the comfort and needs of the patient.

The lower longitudinal edges of foot side portions 62, 64 extend into and are contiguous with the length of a foot bottom portion 66 which during use is positioned directly under the central portion of the length of the user's foot, but is not of sufficient length so as to extend beneath the user's toes or heel. Alternatively, lower foot portion 64 is formed of a separate generally rectangular portion which is connected, for example by stitching or other suitable means, along the sides of the flanking side portions 62, 64.

Best illustrated in FIG. 6 is a sub-layer 68 connected to and disposed beneath foot bottom portion 66. Sub-layer 68 is connected along the sides and front edge to foot bottom portion 66 and is left free at the rearwardly directed edge thereof to provide a pocket shape which is sized and shaped appropriately for snugly sliding receipt of the forwardly directed end of splint foot support portion 22. A substantially rectangular aperture 70 is provided approximately centrally in sub-layer 68 in order to readily accommodate the entire length and width of base plate 26 and the attached key nut 34 which extend downwardly through aperture 70 for manual access.

A particularly preferred feature of the present cover 16 is a foot support pad 72 (indicated in phantom only in FIG. 5) which is sealed within foot portion 66, for example, beneath the thick pile layer which contacts the skin and retained in position by a net or other breathable fabric connected beneath portion 66. Pad 72 is necessarily disposed above foot support portion 22 of splint 12 to serve the purposes thereof. Preferably, pad 72 is formed of a viscoelastic polymeric material, such as that presently commercially available under the trademark AKTON (registered to Action Products, Inc.). In addition to providing the ball of the user's foot with extra protection and comfort during ambulation, support pad 72 also elevates the wearer's foot sufficiently far to aid in the relief of pressure from the wearer's heel. Ideally, the wearer's heel does not touch the interface lining heel area 23. However, should some contact occur, the presence of the interface discourages tissue irritation.

Finally, returning to foot side members 62, 64 of cover 16, each side member extends forwardly, preferably up to but not extending past the position of the wearer's toes. Rearwardly, side members 62, 64 extend along the sides of the wearer's foot and then terminate in upwardly angled strips 74, 76 respectively. Strips 74, 76 continue upwardly and rearwardly sufficiently far to intersect the lower rear edges of leg side portions 58, 56, respectively, where the intersecting edges of the corresponding sections are connected, as by stitching or other equivalent means.

To provide further secure attachment of cover 16 to L-shaped support splint 12, strip 74 terminates in an attached section of conventional hooked fastener material (not seen in the figures) and strip 76 terminates in an attached section of looped fastener material (indicated at 76a in FIG. 5) which material 76a is double-sided with regard to the looped aspect thereof. Thus the double-sided looped strip 76a can be releasably connected to the hooked strip on the opposing side member extension to secure the side members behind the upright portion of the splint. Further, the extreme lower edge of the outwardly facing downwardly extending back leg portion 54 is provided on the inner side thereof with a strip of hooked fastener material for ready and facile attachment to the outward facing side of the double-sided looped fastener strip on connecting fabric strip 74 to prevent the back, bottom, outside edge of cover 16 from flapping loosely, catching objects as the wearer moves about.

Figure 7:
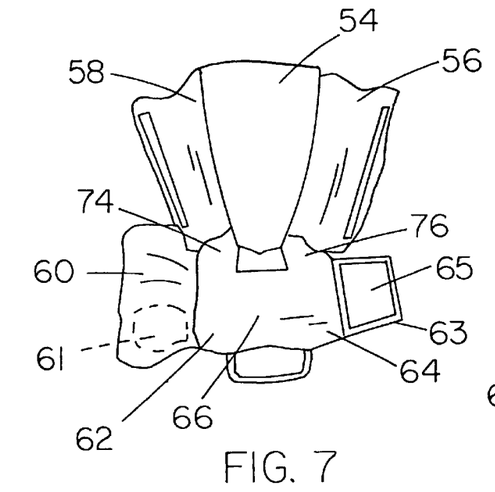
FIGS. 7 through 15 are schematic illustrations showing normal use of the orthotic device of FIG. 1.
Figure 8:
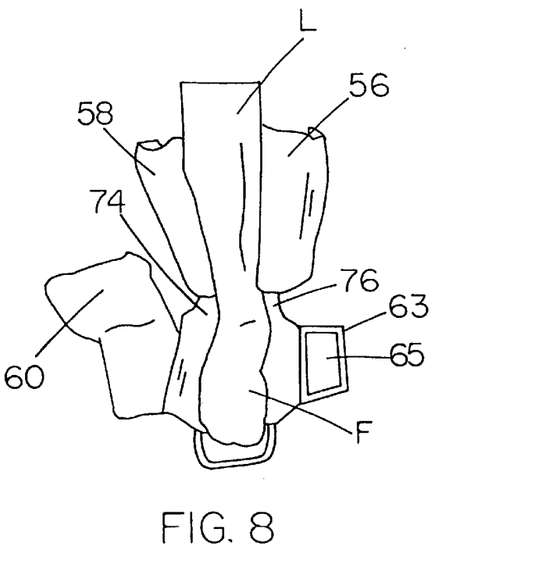
Figure 9:
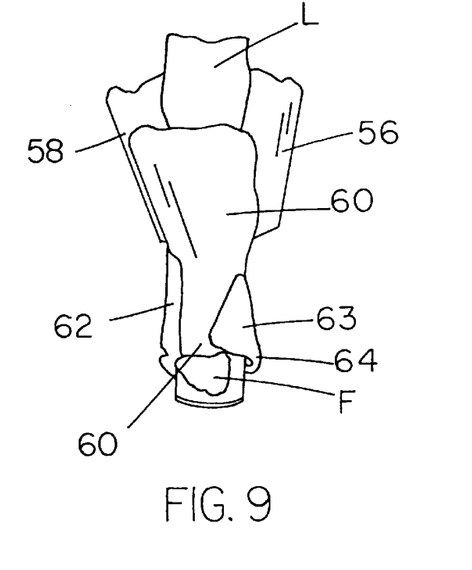

FIGS. 7–15 schematically illustrate typical use of ankle/foot orthosis 10. FIG. 7 shows cover 16 disposed in open position on L-shaped splint 12. FIG. 8 illustrates a wearer placing a foot (generally designated F) and leg (generally designated L) in the orthotic 10. FIG. 9 shows the initial stage of closing the cover 16 to cover the foot and leg, leaving the toe area uncovered.

Figure 10:
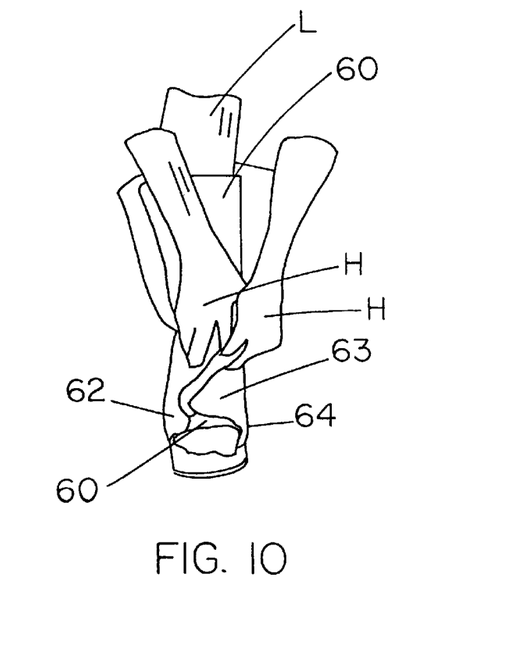
Figures 11, 12, 13, 14, 15:
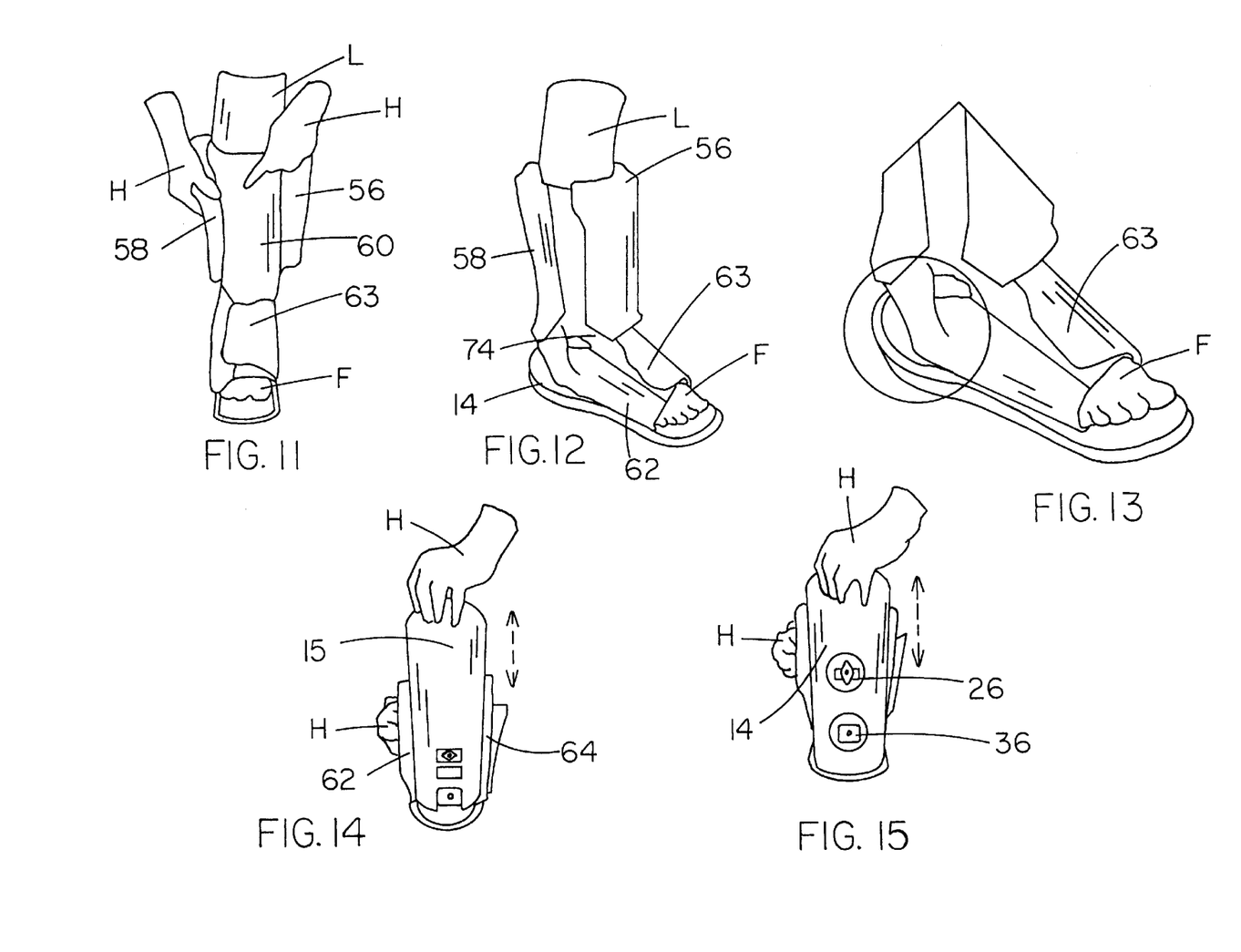

FIG. 10 illustrates the hands (generally designated H) of the user adjusting the foot side portions over the foot in adjustably releasable fashion. FIG. 11 shows the hands of the wearer placing the upper portion of the tongue against the front (shin area) of the lower leg. FIG. 12 shows the leg side portions as the are positioned around and over the tongue portion. FIG. 13 focuses on the heel area, as a reminder in use to check as cover 16 is applied to ensure that the user's heel is clear and free floating (i.e., not in contact with any surfaces) within orthosis 10.

FIG. 14 illustrates connection of the optional toe protector extension to the L-shaped support member 12, after cover 16 is in place. FIG. 15 illustrates placement on support member 12 of walking sole 14 to permit ambulation by the wearer of device 10.

Accordingly it can be seen that the new ankle/foot orthosis as described herein aptly provides heel pressure relief in combination with an integrated anti-microbial, soft interface and an easily removable walker sole. The combination of structural design features described above provides total patient care day or night, regardless of whether the patient is ambulating or at rest.

In view of the foregoing, it will be seen that the several objects of the invention are achieved and other advantages are attained.

Although the foregoing includes a description of the best mode contemplated for carrying out the invention, various modifications are conceivable.

As various modifications could be made in the constructions herein described and illustrated without departing from the scope of the invention, it is intended that all matter contained in the foregoing description or shown in the accompanying drawings shall be interpreted as illustrative rather than limiting.

What is claimed is:

1. A foot and ankle orthosis which is adapted for use by a patient in both resting and walking modes, the orthosis comprising:

a generally L-shaped support member which has a leg portion positioned behind the patient's lower leg, a heel portion positioned behind the patient's heel and Achilles' tendon area, and a foot portion positioned substantially entirely against the sole of the patient's foot when the orthosis is in the normal, operative use position, the foot portion having an upper surface and a lower surface and the heel portion connecting the leg portion and the foot portion;

a walking sole plate which is releasably connectable to the generally L-shaped support member, to thereby permit optional use by the patient of the walking sole plate in combination with the generally L-shaped support member for facilitating ambulation by the patient;

a manually operable locking mechanism attached to the lower surface of the foot portion of the generally L-shaped support member, to thereby permit rapid, selectively releasable connection of the walking sole plate to the generally L-shaped support member, wherein the manually operable locking mechanism attached to the bottom surface of the foot portion of the L-shaped support member includes a first base plate and a second base plate, the first base plate and the second base plate being fixed to the lower surface of the semi-rigid foot bed and positioned substantially parallel to each other and transversely with respect to the longitudinal axis of the semi-rigid foot bed, the first base plate being disposed forwardly of the second base plate, a connecting plate fixed to the second base plate and extending outwardly and rearwardly therefrom, thereby defining a space between the lower surface of the semi-rigid foot bed and an upper surface of the connecting plate to receive and retain a portion of the semi-rigid foot bed of the walking sole plate, and a key nut rotatably connected to the first base plate and extending outwardly therefrom to further retain the semi-rigid foot bed in position for selective operative use of the walking sole plate and to permit ready, manual release of the walking sole plate from an operative position thereof; and means for connecting the orthosis to the patient's foot and leg.

2. The orthosis of claim 1, wherein the generally L-shaped support member has an inside surface, which receives the foot and leg of the patient, and an outside surface, and further wherein the inside surface of at least the foot portion of the generally L-shaped member is overlayered with a soft, pliable interface, to thereby cushion pressure on the sole of the foot during ambulation by the patient.

3. The orthosis of claim 2, wherein the, soft, pliable interface of the generally L-shaped support member is formed of an anti-microbial material.

4. The orthosis of claim 2, wherein the cushioning interface has a uniform thickness and is laminated onto the inside surface of the generally L-shaped member.

5. The orthosis of claim 1, wherein the heel portion of the generally L-shaped support member curves rearwardly and outwardly away from the longitudinal axis of the leg portion of the generally L-shaped support member to such an extent that when the orthosis is in normal use position no pressure is placed on the heel of the patient by the heel portion of the orthosis.

6. The orthosis of claim 1, wherein the walking sole plate comprises a semi-rigid elongated foot bed which is substantially flat, except for an upturned portion at an end of the foot bed, and having an upper surface and a lower surface, and an outer layer of cushioning, material connected to the lower surface of the foot bed, to thereby enhance ambulation by the patient wearing the orthosis, and the semi-rigid foot bed being adapted for connection to the generally L-shaped support member.

7. The orthosis of claim 6, wherein the substantially flat, semi-rigid foot bed defines at least one aperture sized and positioned appropriately for receipt of the locking mechanism connected to the lower surface of the foot portion of the generally L-shaped support member.

8. The orthosis of claim 7, wherein the outer layer of cushioning, material defines at least one opening sized and positioned appropriately to surround the at least one aperture in the semi-rigid foot bed and permit manually operative access thereto.

9. The orthosis of claim 6, wherein the outer layer of cushioning material includes a non-slip surface over at least a portion of the surface area of the outer layer of cushioning material.

10. The foot and ankle orthosis of claim 6, wherein the upturned portion at an end of the foot bed of the walking sole plate has an overlayer of soft material to provide cushioning for the patient's toes during ambulation while wearing the orthosis.

11. The orthosis of claim 1, wherein the means for connecting the orthosis to the patient's foot and leg is a cover which is positionable substantially entirely over the generally L-shaped support member when the walking sole plate is not connected thereto, the cover being adjustably connectable around the patient's foot and leg when the cover is positioned on the generally L-shaped support member, the cover further being soft and thick, to protect the patient's foot, ankle and lower leg from contact with the generally L-shaped support member regardless of whether the walking sole plate is connected to the generally L-shaped support member.

12. The orthosis of claim 11, wherein the cover is formed of a plurality of flexible material sections connected together as a single unit shaped to cover substantially entirely all of the patient's foot, but leaving the toes free and unencumbered.

13. The orthosis of claim 12, wherein the cover further comprises an elongated, longitudinally disposed back leg section, at least one side leg section connected to the back leg section, a bottom foot section, at least two side foot sections connected to the bottom foot section, and a tongue section permanently connected to one of the side foot sections and being releasably, adjustably connectable to the at least one side leg section and to the other side foot section, to thereby permit comfortable, adjustable securement of the patient's foot and leg to the orthosis.

14. The orthosis of claim 13, wherein the back leg section has a first longitudinal side edge and a second longitudinal side edge, and the at least one side leg section is a first side leg section and a second side leg section, each of the first side leg section and the second side leg section having a front edge and a rear edge, the first side leg section and the second side leg section being connected along corresponding rear edges thereof to opposed longitudinal side edges of the back leg section and extending forwardly therefrom.

15. The orthosis of claim 10, wherein each of the side foot sections has a connecting strip which extends rearwardly and is connected to the back leg section on lower ends of the first longitudinal side edge and the second longitudinal side edge thereof.

16. The orthosis of claim 13, wherein the tongue section has a leg portion and a foot portion, both the leg portion and the foot portion of the tongue section having an external surface, the external surface of the leg portion being covered entirely with the looped part of hook and loop fastener material, and the at least one side leg section being provided with a longitudinal strip of the hooked part of hook and loop fastener material to thereby permit adjustable, releasable connection of the at least one side leg section to the tongue.

17. The orthosis of claim 13, wherein the tongue section of the cover has a leg portion and a foot portion, both the leg portion and the foot portion having an external surface, the external surface of the foot portion of the tongue section being substantially entirely covered with the hook part of hook and loop fastener material, and at least one of the side foot sections of the cover having on the external surface thereof the loop part of hook and loop fastener material, to thereby.

18. The orthosis of claim 13, wherein the cover further comprises a sublayer of material which is disposed beneath the foot section and connected to a plurality of sides thereof, to thereby form a space between the bottom foot section and the sublayer for sliding receipt of at least a front edge of the foot portion of the generally L-shaped support member.

19. The orthosis of claim 18, wherein the sublayer of material defines an aperture which is configured and positioned appropriately for receipt and extension therethrough of at least a portion of the manually operable locking mechanism.

20. The foot and ankle orthosis of claim 1, and further comprising an extension plate which can be optionally interchanged with the walking sole plate, the extension plate having a length which is at least as long as a length of the walking sole plate and which when in normal use position extends beyond the end of the patient's toes so as to provide protection of the patient's toes from contact with bed covers and other objects when the patient is not ambulatory.

21. The combination of a foot and ankle orthosis, and a cover for the foot and ankle orthosis to hold the orthosis in place on a patient's foot and lower leg and to relieve pressure from the material of the orthosis against the tissue of the patient's foot and lower leg, wherein the orthosis comprises a generally L-shaped support member which, when the orthosis is in normal use position, has a leg portion positioned behind the patient's lower leg, a heel portion positioned behind the patient's heel and Achilles' tendon area, and a foot portion positioned substantially entirely against the sole of the patient's foot, the foot portion having an upper surface and a lower surface;

a walking sole plate which is releasably connectable to the generally L-shaped support member, to thereby permit optional use by the patient of the walking sole plate in combination with the generally L-shaped support member for facilitating ambulation by the patient;

a manually operable locking mechanism attached to the lower surface of the foot portion of the generally L-shaped support member, to thereby permit rapid, selectively; releasable connection of the walking sole plate to the generally L-shaped support member, wherein the manually operable locking mechanism attached to the bottom surface of the foot portion of the L-shaped support member includes a first base plate and a second base plate, the first base plate and the second base plate being fixed to the lower surface of the semi-rigid foot bed and positioned substantially parallel to each other and transversely with respect to the longitudinal axis of the semi-rigid foot bed, the first base plate being disposed forwardly of the second base plate, a connecting plate fixed to the second base plate and extending outwardly and rearwardly therefrom, thereby defining a space between the lower surface of the semi-rigid foot bed and an upper surface of the connecting plate to receive and retain a portion of the semi-rigid foot bed of the walking sole plate, and a key nut rotatably connected to the first base plate and extending outwardly therefrom to further retain the semi-rigid foot bed in position for selective operative use of the walking sole plate and to permit ready, manual release of the walking sole plate from an operative position thereof; and further wherein the cover comprises a plurality of flexible material sections connected together as a single unit shaped to cover substantially all of the patient's foot, but leaving the toes free and unencumbered.

* * * * *

UNITED STATES PATENT AND TRADEMARK OFFICE
CERTIFICATE OF CORRECTION

PATENT NO : 5,961,477
DATED : October 5, 1999
INVENTOR(S): Turtzo, Craig H.

It is certified that error appears in the above-identified patent and that said Letters Patent is hereby corrected as shown below:

Column 5, Line 4, change "comers" to --corners--.

Column 8, Line 65, after "foot portions 60, 62" change "and" (first occurrence) to --can--.

Column 10, Line 11, after "side portions as" change "the" (first occurence) to --they--.

IN THE CLAIMS:

Column 12, Claim 15, Line 37, replace "10" with --14--.

Signed and Sealed this

Twenty-third Day of May, 2000

*Attest:*

Q. TODD DICKINSON

*Attesting Officer*      *Director of Patents and Trademarks*